(12) United States Patent
Yamakawa et al.

(10) Patent No.: US 7,118,662 B2
(45) Date of Patent: Oct. 10, 2006

(54) ELECTROPHORESIS APPARATUS

(75) Inventors: Hironobu Yamakawa, Chiyoda (JP); Ryo Miyake, Tsukuba (JP); Yasuhiko Sasaki, Tsuchiura (JP); Akira Koide, Azuma (JP)

(73) Assignee: Hitachi, Ltd., Tokyo (JP)

( * ) Notice: Subject to any disclaimer, the term of this patent is extended or adjusted under 35 U.S.C. 154(b) by 328 days.

(21) Appl. No.: 10/041,597

(22) Filed: Jan. 10, 2002

(65) Prior Publication Data

US 2002/0096432 A1    Jul. 25, 2002

(30) Foreign Application Priority Data

Jan. 19, 2001  (JP)  ............................. 2001-010980

(51) Int. Cl.
  *G01N 27/447*  (2006.01)
  *G01N 27/26*   (2006.01)

(52) U.S. Cl. .................. 204/603; 204/601; 204/612; 204/451; 204/452; 204/461

(58) Field of Classification Search ................ 204/601, 204/603, 612, 451, 452, 461
See application file for complete search history.

(56) References Cited

U.S. PATENT DOCUMENTS

| | | | |
|---|---|---|---|
| 5,062,942 A * | 11/1991 | Kambara et al. ............ 204/612 |
| 5,268,080 A * | 12/1993 | Kambara et al. ............ 204/461 |
| 6,017,765 A * | 1/2000  | Yamada et al. ............ 623/1.15 |
| 6,361,672 B1 * | 3/2002 | Zhu et al. .................... 204/603 |
| 6,485,625 B1 * | 11/2002 | Simpson et al. ............ 204/601 |
| 6,576,108 B1 * | 6/2003 | Takahashi et al. .......... 204/603 |
| 6,627,433 B1 * | 9/2003 | Frazier et al. ............ 435/288.7 |

| | | | |
|---|---|---|---|
| 2004/0007465 A1 * | 1/2004 | Goldberg et el. ........... 204/452 |

FOREIGN PATENT DOCUMENTS

| | | | |
|---|---|---|---|
| JP | 5-296978 A    | * | 11/1993 |
| JP | 9-15205 A     | * | 1/1997  |
| JP | 9-288089 A    | * | 11/1997 |
| JP | 9-288090 A    | * | 11/1997 |
| JP | 11-352102 A   | * | 12/1999 |
| JP | 2001-83118 A  | * | 3/2001  |
| JP | 2001-330587 A | * | 11/2001 |
| WO | WO 00/069996 A1 | * | 2/2000 |

* cited by examiner

OTHER PUBLICATIONS

Ultra-high-speed DNA fragment separations using microfabricated capillary array electrophoresis chips (A.T.Woolley et. al, Proc.Natl., 1994 vol. 91, 11348-11352.

*Primary Examiner*—Alan Diamond
(74) *Attorney, Agent, or Firm*—Antonelli, Terry, Stout and Kraus, LLP.

(57) ABSTRACT

The windows 5a, 5b are configured so that the thickness of the upper and lower parts of the substrate formed therein with the channels becomes thinner in these parts than in other parts. An air space is defined in the vicinity of the one side wall of the channel within a part where the first outgoing window 5a is formed, so as to serve as a window, and the second outgoing window 5b has a shape such as to be recessed inward from the one side wall of the planar plate 10, in comparison with the other part thereof. Further, the fluorescence transmission path 6b is also formed on opposite sides with air spaces. It is noted that a rod-like fiber or the like may be embedded in the planar plate 10 on the outgoing side of the planar plate 10 at the time of forming the separation channel 21 and the like.

28 Claims, 7 Drawing Sheets

ELECTROPHORESIS APPARATUS

BACKGROUND OF THE INVENTION

The present invention relates to an electrophoresis apparatus adapted to be used for analyzing protein, peptide, amino acid, neurotransmitter, hormone nucleic acid or the like which is contained in organisms, or a trace substance contained in the environment, foods, chemical or the like.

RELATED ART

There has been proposed a technology of electrophoretic separation which is carried out in channels in a planar plate as disclosed in "Ultra-high speed DNA fragment separations using microfabricated capillary array electrophoresis chips" by A. T. Woolley et al, Proc. Natl., 1994, Vol. 91, pages 11348–11352. The device disclosed in this document is composed of two thin planar glass plates which are joined together and one of which is formed therein with a plurality of fine grooves fabricated by etching so as to define channels together with the other planar glass plate matched with the former. These channels include a sample channel for introducing a sample, and a separation channel crossing the former, for separating the sample. Holes are formed at opposites ends of the sample channel and the separation channels so as to serve as solution reservoirs in which electrodes are inserted, respectively.

The above-mentioned device of prior art is operated as follows: a high voltage is applied between the electrodes inserted in the solution reservoirs at opposite ends of the sample channel so as to introduce a sample into a channel crossing part between the sample channel and the associated separation channel. Then, a voltage is applied between the electrodes inserted in the solution reservoirs at opposite end of the separation channel so as to extract only a sample located in the channel crossing part, into the separation channel where the electrophoresis of the sample is carried. In the sample which is a mixed solution composed of several components, the components are separated from one another with the use of differences among electrophoretic speeds which are caused by their different charge states and different interactions with respect to a separating medium solution. A laser beam is irradiated onto the separation channel from a position above the planar glass plates. Excited light from the sample in the separation channel is detected by a detector which is arranged, coaxial with the laser beam, above the planar glass plates.

The above-mentioned channels are arranged in a planar plate in parallel with one another in the form of an array, and several examinations can be once made by scanning the channels with the leaser beam.

By the way, in the above-mentioned prior art, an electrophoresis substrate is made of a very thin planer glass plate having a thickness of about 0.2 to 0.3 mm. Accordingly, the incoming light and the outgoing light are limited in a direction orthogonal to the planar plate. Further, the channels are usually formed by etching with the use of fluorinated acid. Accordingly, the bottoms of the channels cannot be safely said to be flat and smooth. Accordingly, the irradiation of a beam and the detection of fluorescence are usually carried out in one and the same direction above the planar plate. Due to such a limitation caused by the optical system, there have been raised such problems of deteriorating the S/N ratio caused by background light such as scattered light or stray light, and lowering the accuracy of detection.

Further, in the above-mentioned prior art, since several channels are formed in one and the same planar plate in the form of an array in order to carry out several examinations at one time, and accordingly, a laser beam should be irradiated onto the channels one by one. Thus, the time of irradiation of the laser beam onto each of the channels becomes shorter, and accordingly, a sample therein cannot be fully excited so that sufficient detection sensitivity would be unavailable. Further, there would be raised such problem that a variation in the time of fluorescence cannot be detected on a real time base. Further, the provision of a movable mirror and a complicated optical system are inevitably required for scanning with a laser beam, thereby it would cause the apparatus to be expensive and large-sized

SUMMARY OF THE INVENTION

The present invention is devised in view of the above-mentioned problems inherent to the prior art, and accordingly, a first object of the present invention is to provide an electrophoresis apparatus which can reduce affection by background light or stray light so as to enhance the accuracy of detection.

A second object of the present invention is to provide an electrophoresis apparatus which can easily analyze samples from several specimens at a high speed.

In order to achieve the first object, according to the present invention, there is provided an electrophoresis apparatus comprising a planar plate formed therein with a channel for electrophoretic separation, a light irradiating means for irradiating an excitation beam into a detection part formed in a part of the channel, a fluorescence detecting means for detecting a degree of fluorescence which is generated from a sample by the excitation beam, the channel having a rectangular cross-sectional shape and being composed of a top surface and a bottom surface which are parallel with the surface of the planar plate, and left and right side wall surfaces, a first incoming window which is flat and smooth and which is formed in the bottom surface of the channel in the detecting part, for introducing the excitation into the channel, a second flat and smooth incoming window which is formed on a surface of the planar plate which is opposed to the first incoming window, an excitation transmission path formed between the first and second incoming windows, a first outgoing window formed in one of the side wall surfaces of the channel and a second outgoing window formed in a side surface of the planar plate at a position opposed to the first outgoing window, and a fluorescent transmission path between the first outgoing window and the second outgoing window.

In order to achieve the second object, according to the present invention, there is provided an electrophoresis apparatus comprising a plurality of flat plates each formed therein with a capillary channel and each having the same configuration as the above-mentioned planar plate, which are layered one upon another so that the channels in the planar plates are overlapped with one another, a light beam irradiating means for irradiating a single excitation beam, which is provided at a position where the light beam goes through the capillary channels in the plurality of planar plates, at the same time, and fluorescence detecting means located at positions in extension of outgoing windows formed in side surfaces of the planar plates.

Next, explanation will be hereinbelow made of preferred embodiments of the present invention with reference to the accompanying drawings among which:

DESCRIPTION OF THE PREFERRED EMBODIMENTS OF THE INVENTION

Figure 1:
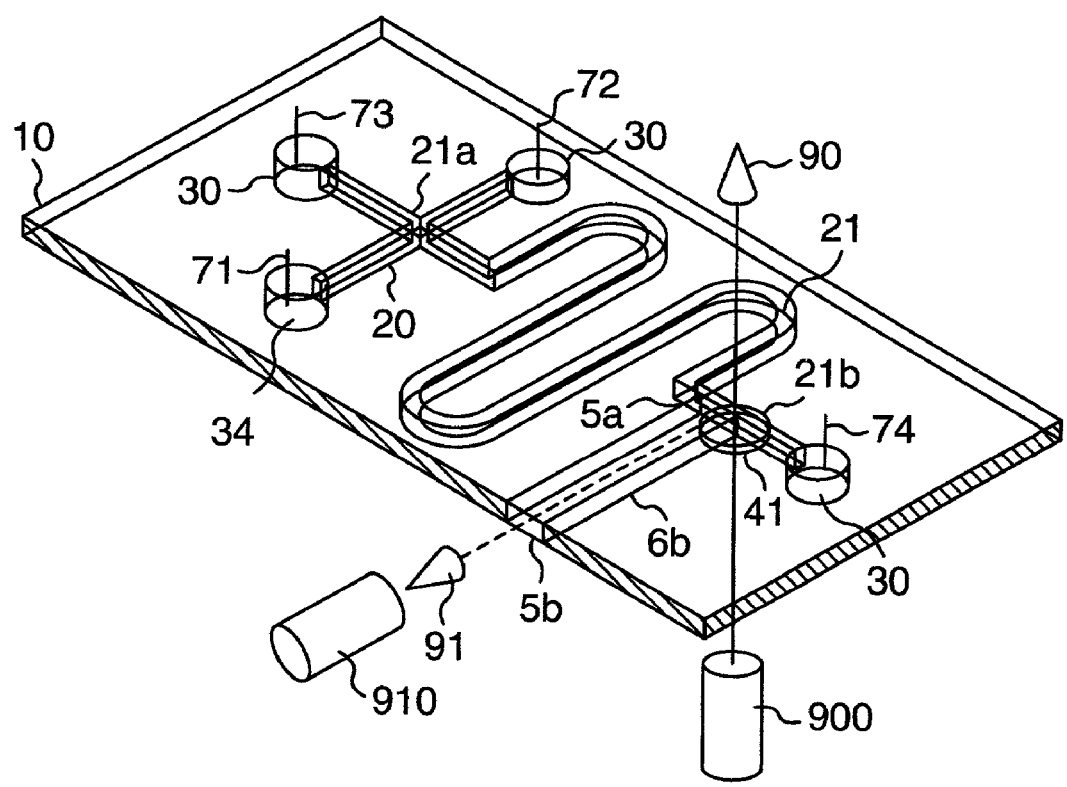
FIG. 1 is a perspective view illustrating an embodiment of the present invention.

Referring to FIG. 1 which is a perspective view illustrating a channel substrate in an electrophoresis apparatus in an embodiment of the present invention, a planar plate 10 is formed therein with sample channels 20, a separation channel 21, solution reservoirs 30, a sample reservoir 34 and the like. A detecting part 21b is formed, intermediate of the separation channel 21. The separation channel 21 has a bottom part formed therein with an incoming window through which a light beam can be readily introduced into the detecting part 21b from an excitation light source 900. One side wall of the separation channel 21 is formed therein with a first smooth outgoing window 5a through which light can readily be led into the planar plate 10, and a fluorescence transmission path 6b for transmitting fluorescence toward one side of the planar plate 10 while preventing the fluorescence from leaking is extended from the first outgoing window 5a to the one side of the planar plate 10, and is terminated with its output part at one side of the planar plate 10, where a second smooth outgoing window 5b is formed. Further, a fluorescence detector 910 is arranged on the outside of the second outgoing window 5b.

The windows 5a, 5b are configured so that the thickness of the upper and lower parts of the substrate formed therein with the channels becomes thinner in these parts than in other parts. An air space is defined in the vicinity of the one side wall of the channel within a part where the first outgoing window 5a is formed, so as to serve as a window, and the second outgoing window 5b has a shape such as to be recessed inward from the one side wall of the planar plate 10, in comparison with the other part thereof. Further, the fluorescence transmission path 6b is also formed on opposite sides with air spaces. It is noted that a rod-like fiber or the like may be embedded in the planar plate 10, on the outgoing side of the planar plate 10 at the time of forming the separation channel 21 and the like.

The solution reservoirs 30 and the sample reservoir 34 are inserted therein with electrodes, that is, first and second sample introducing electrodes 71, 72, and third and fourth sample separating electrodes 73, 74. A light converging lens 41 is provided between the outgoing window for the detection part and the separation channel 21. It is noted that a cover of a transparent planar plate (which is not shown) is provided on the top of the planar plate 10 formed therein with the channels although FIG. 1 shows such a condition that the top side of the planar plate 10 is opened.

The operation of the electrophoresis apparatus having the above-mentioned configuration will be described hereinbelow.

A separation medium solution is poured in the solution reservoirs 30 until both sample channel 20 and separation channel 34 are filled therein with the solution. A sample is, at first, dripped into the sample reservoir 34 and thereafter a voltage is applied between the first and second electrodes 71, 72 at both ends of the sample channel 20 so as to produce an electrical field in the channel 20. The electrical field is effected so as to cause electrophoresis of the sample until the leading end of the sample comes to a position downstream of a channel crossing part 21a. Then, a voltage is applied between the third and fourth electrodes 73, 74 at both ends of the separation channel 21 so as to introduce the sample from the channel crossing part 21a into the separation channel 21 in order to initiate the separation of the sample.

The sample is separated into components due to electrophoretic speeds which are different from one another among the components while the sample is led to a detecting part 21b. An excitation beam 90 is irradiated to the detecting part 21b from the excitation light source 900. Fluorescence 91 which is emitted from the sample in response to the excitation beam 90 is transmitted through the fluorescence outgoing window 5a, the fluorescence transmission path 6b and the fluorescence outgoing window 5b, and is received by the detector. There may be used a laser, a light emitting diode, a halogen lamp or the like for the excitation beam. As to the detector, an array of photo-sensors for obtaining signals from respective channels, a cooled type CCD camera having pixel elements for obtaining fluorescent signals from channels in a wide range or the like may be used, which is selected in view of a kind of a sample, and a wavelength.

In this embodiment, the apparatus is formed therewith the incoming window for introducing the excitation beam which is irradiated underneath the apparatus. Accordingly, scattering of light and lowering of the intensity of light can hardly occur so that the excitation beam can be prevented from scattering and lowering the light intensity thereof even though it passes through a side wall of the channel, thereby it is possible to efficiently excite fluorescence from the sample. In order to allow the fluorescence produced from the sample to laterally outgo, there are provided the first outgoing window, the light transmission path and the second outgoing window. Thus, no occurrence of scattering of light and lowering of the light intensity is caused at a side surface of the channel. The light receiving surface of the detector is located at one side surface of the apparatus, and accordingly, the excitation beam which causes noise during detection can be prevented from being incident upon the detector, thereby it is possible to enhance the S/N ratio. In view of the effects as mentioned above, the accuracy of detection can be enhanced.

In this embodiment, the light transmission path which is transparent is provided in a part of the planar plate 10. However, the planar plate 10 may be made of a transparent material in its entirety. With this configuration in which the planar plate 10 is made of the transparent material, a part in the planar plate 10 itself can serve as the light transmission path.

Figure 2:
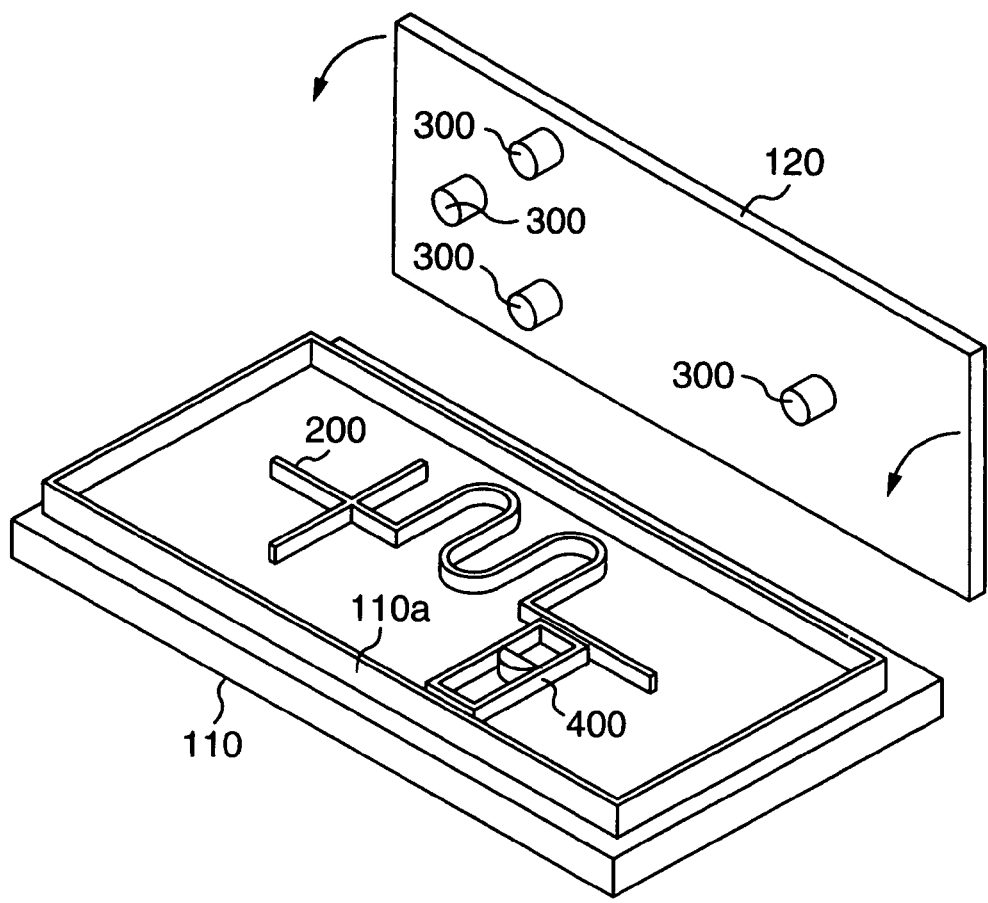
FIG. 2 is a perspective view for explaining a method of manufacturing an electrophoresis substrate shown in FIG. 1.

Explanation will be made of a method of manufacturing the electrophoresis substrate with reference to FIG. 2 which shows a mold for forming the electrophoresis substrate shown in FIG. 1. Referring to FIG. 2, the mold is composed of a first plate 110 having a frame 110a and provided with a rectangular male die 200 for forming the capillary channels, and a female die 400 for forming the fluorescence converging lens and the first and second fluorescence outgoing window, and a second plate 120 provided with a male die 300 for forming the sample reservoir and solution reservoirs. The second plate 120 is fitted in the frame 110a of the first plane 110 when the substrate is molded. These plates may be formed by cutting metal stocks, or etching single crystal silicon plates. Further, the male and female dies may be formed on planar plates by electric spark machining. Further, deep groove-like resists are formed by X-ray lithography, and are then subjected to Ni-plating so as to form nickel structure members after the resists are removed, and the thus formed structure members may be used for the mold.

The above-mentioned mold is coated thereover with thermosetting transparent epoxy resin or silicon elastomer polydimethylsiloxane in order to transfer a fine structure. The thus formed transferred plate is joined with a transparent plate so as to obtain the electrophoresis substrate incorporating the capillary channels.

Figure 3:
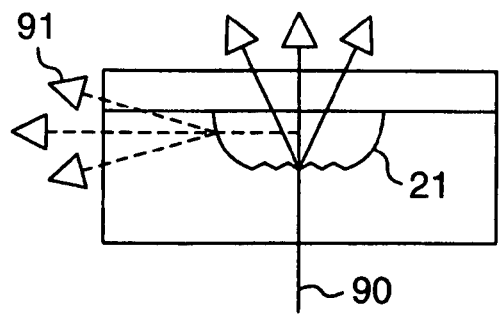
FIG. 3 is a sectional view illustrating a separation channel which is formed by etching a glass pane and which is in such a condition that an excitation beam is irradiated onto the separation channel.

FIG. 3 shows a conventional channel structure formed by etching a glass plate, in which the channel has a curvilinear cross-sectional shape. With the use of the above-mentioned mold, the channel in this embodiment of the present invention can have a rectangular cross-sectional shape, in stead of the curvilinear cross-sectional shape formed by etching the glass plate. Further, optical components including the light incoming window and the fluorescence outgoing windows can be integrally molded. Thus, analysis with a high degree of accuracy can be made with no refraction of an excitation beam and fluorescence, without decaying the light intensity thereof due to scattering.

Next explanation will be made of a method of forming the electrophoresis substrate with the use of a photosensitive resin film for the above-mentioned mold. Photolithography including an exposure step and a baking step is used so as to form a mold made of the photosensitive resin film. The thus formed mold is coated thereover with silicon elastomer polydimethylsiloxane so as to transfer a fine structure in order to form the channels. However, the thus formed channels have side surfaces and bottom surfaces which are in general unsatisfactorily smooth, and are insufficient for optical detection.

In view of this fact, the applicants found a condition which can enhance the smoothness of side surfaces in the mold made of the photosensitive resin film by optimizing process conditions.

Figure 4:
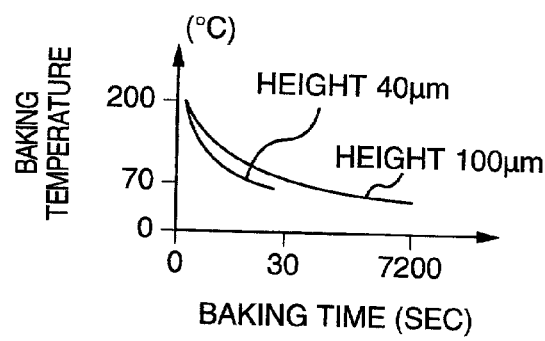
FIG. 4 is a view for explaining conditions in one embodiment of the manufacturing method.

FIG. 4 shows a graph which exhibits conditions as to the time of a baking process and the temperature of baking. Further, during the exposure process a reduction type exposure apparatus such as a stepper is used. From FIG. 4, a baking time and a baking temperature can be optimumly set with the height (for example, 40 μm or 100 μm) of the mold as a parameter. By applying this optimum condition, the resist structure members having side surfaces which are satisfactorily smooth can be formed.

The light transmission characteristics of side walls of channels which are formed by transfer onto the silicon elastomer polydimethylsiloxinane material by using a photosensitive resin film having smooth side surfaces for the mold, and of walls surfaces of the planar plate were evaluated. As a result, it was found that substantially no decay and scattering of light occurs. Thus, the detection with a high degree of accuracy can be made.

Figure 5:
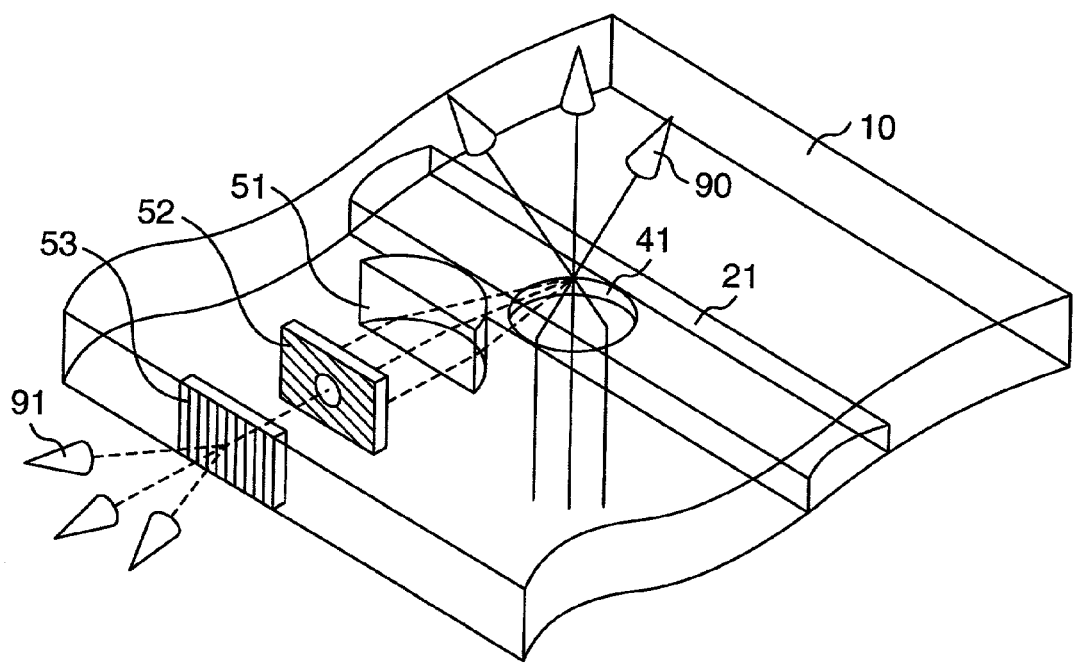
FIG. 5 is an enlarged view illustrating another example of the separation channel in a part around a detection part.

FIG. 5 is an enlarged view illustrating a separation channel 21 in a part around the detecting part in another embodiment of the present invention. An excitation focusing lens 41 for the excitation beam 90 is located in the planar plate underneath the separation channel 21. A fluorescence collesting lens 51, a spatial filter 52 and grating 53 for fluorescence 91 are arranged in the planar plate. These optical component parts are integrally incorporated in the planar plate with the use of a polymer material such as epoxy resin or polydimethylsiloxane, which has satisfactory transcription, as a transparent member.

In this embodiment, since the optical component parts for the excitation beam and the fluorescence are formed in the planar plate, no optical alignment is required, and accordingly, it is possible to prevent scattering and decay of light at a side surface of a channel. With the above-mentioned technical effects, the degree of accuracy for the detection can be enhanced.

Figure 6:
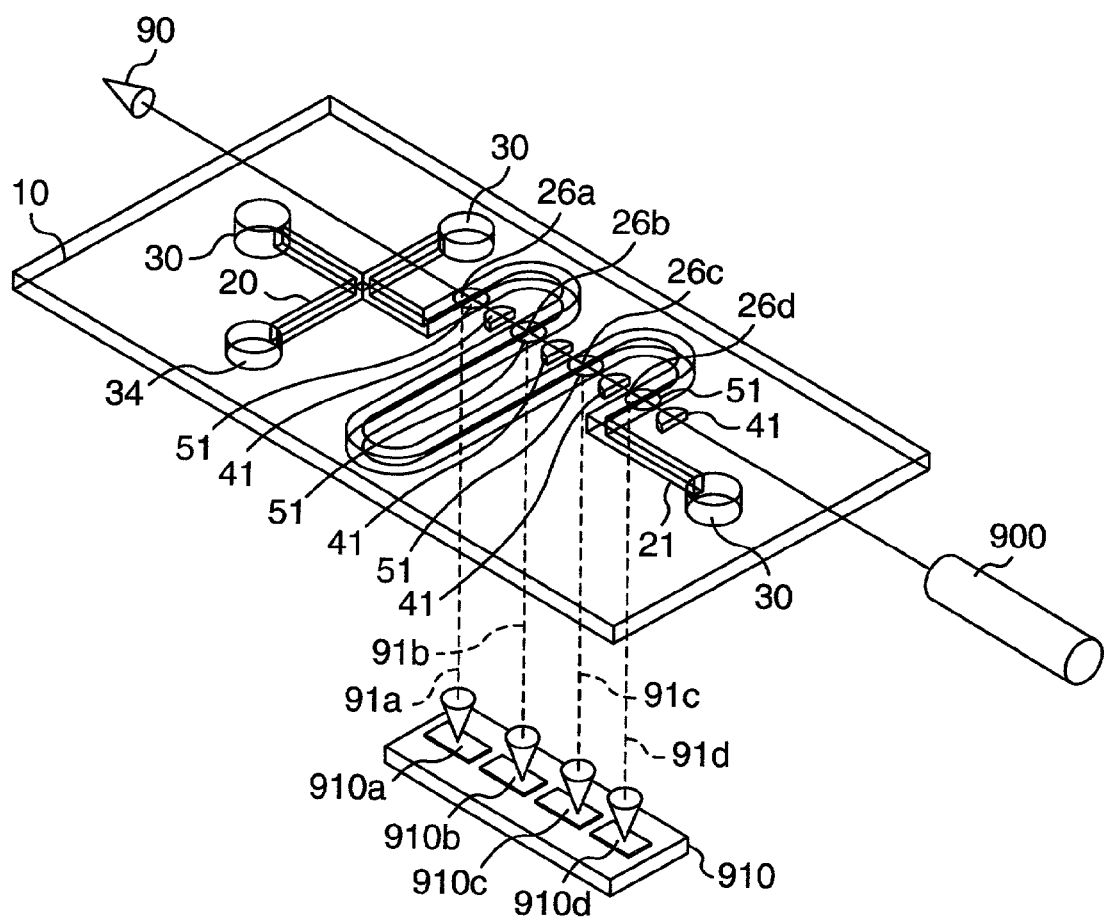
FIG. 6 is a perspective view illustrating a variant form of the embodiment of the present invention.

FIG. 6 shows a variant form of the embodiment of the electrophoresis channel substrate according to the present invention. The electrophoresis substrate is the same as that shown in FIG. 1, except that the separation of a sample is detected by using a curve of the separation channel. That is, an excitation source is located on one side of the substrate in the flowing direction, and the excitation beam 90 is irradiated in a transverse direction of the substrate so as to allow the light beam to be incident upon one side of the separation channel 21 while fluorescence is emitted from the bottom (or top) side of the separation channel. With this arrangement, fluorescence is detected at a plurality of positions in the separation channel 21. An excitation focusing lens 41 is provided, near to a side surface of the separation channel 21, and a fluorescence collecting lens 51 is provided in the bottom part of the separation channel 21.

The operation of the above-mentioned configuration will be hereinbelow explained. A plurality of positions to which an excitation beam is irradiated, such as irradiation points 26a, 26b, 26c, 26d, are provided in the separation channel 21. Emissions 91a, 91b, 91c, 91d of fluorescence from these irradiation points 26a, 26b, 26c, 26d, are detected respectively by detection parts 910a, 910b, 910c, and 910d on the fluorescence detector 910. As to the excitation source 900 and the fluorescence detector 910, there may be used those explained in the previous embodiment.

In this embodiment, since no excitation beam 90 is incident upon the fluorescence detector 910, stray light and background light can be reduced, thereby it is possible to enhance the degree of accuracy for the detection. With a certain sample, the separation would be completed not only around the irradiation point 26d in the vicinity of the terminal end of the separation channel 21, but also around the irradiation point 26a or 26b in the separation channel 21. In this case, according to the configuration of this embodiment, the completion of the separation can be detected by the detecting part 910a or the like underneath the irradiation points. Thereby, it is possible to speed up the analysis.

Figure 7:
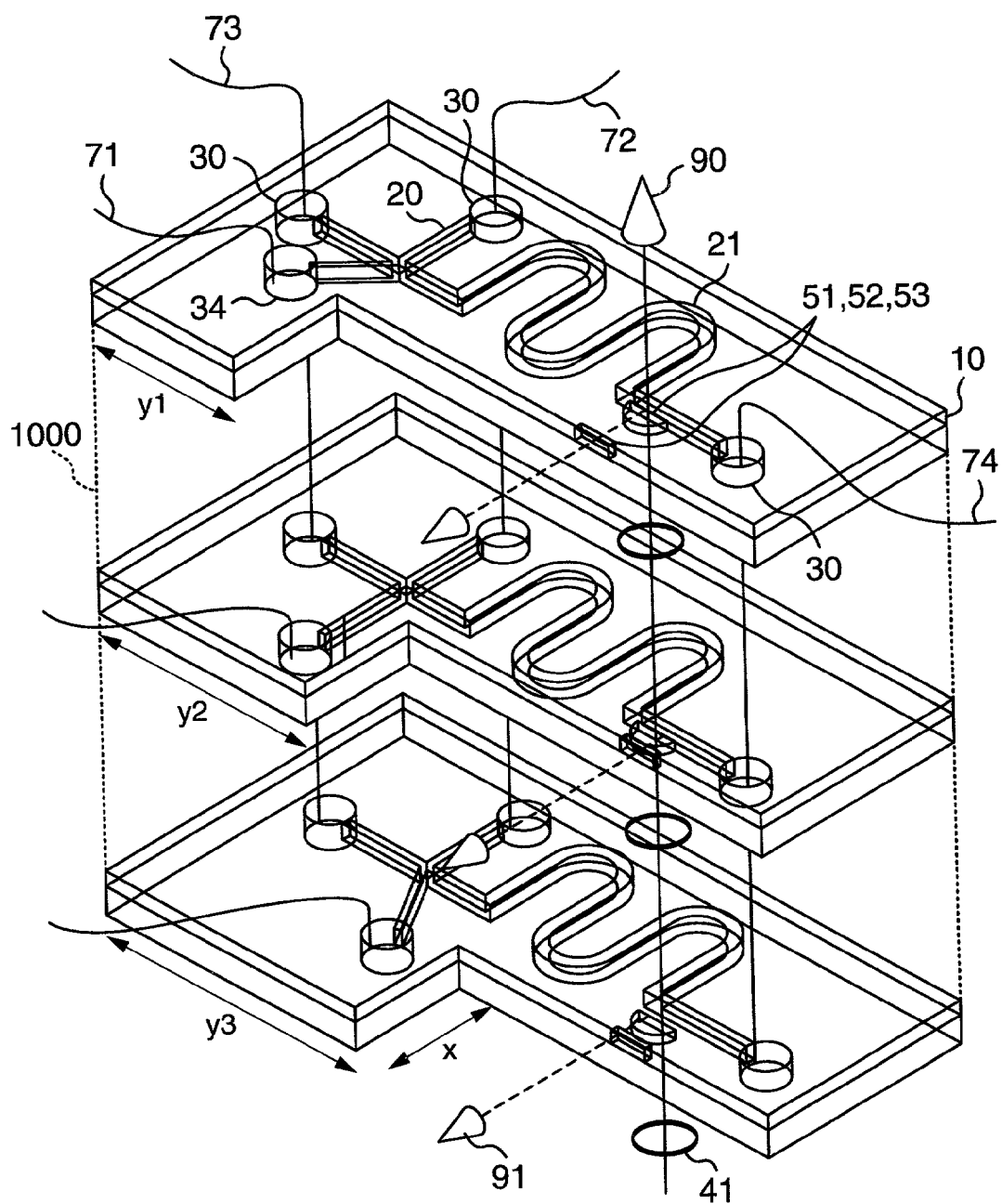
FIG. 7 is a perspective view illustrating another variant form of the embodiment of the present invention.

FIG. 7 shows another variant form of the embodiment according to the present invention. In this variant form, the electrophoresis substrates each of which is shown in FIG. 1 are stacked one upon another in multi-stages. In each planar plate 10, there are provided a sample channel 20, a separation channel 21, solution reservoirs 30, a sample reservoir 34, an excitation focusing lens 41, a fluorescence collecting lens 51, a spatial filter 52 and grating 53. In this variant form, although the planar plates are layered in three stages, they may be layered up more than three stages, and as well they may be layered up two stages. The planar plates are layered one another so as to obtain a channel assembly 1000. The excitation beam 90 can be simultaneously irradiated to the separation channels 21 in all planar plates. The solution reservoirs 30 having three in each of the planar plates are formed, piercing through all planar plates. With this arrangement, separation medium is poured into the topmost solution reservoirs 30 so as to fill the separation medium in the sample channels 20 and the separation channels 21 in all planar plates. Further, the solution reservoirs 30 serve as holes for receiving electrodes 72, 73, 74, respectively. The planar plate 10 at each stage is cut off while a part having a predetermined length, for example, y1, y2 or y3 in the direction of the separation channel 21 and a predetermined length. for example. x1, x2 or x3 in the direction of the sample channel is left in the planar plate. The length X of the cut-off part is uniform among the planar plates layered in the three stages. The distance by which the fluorescence 91 advances through the planar plate is different by the length X among the planar plates layered in three stages, and accordingly, the attenuation and scattering of light can be reduced. The lengths y1, y2, y3 become longer and longer one by one in the mentioned order, and accordingly, the respective sample reservoirs 34 are not extended through all planar plates but are independent from one another among the planer plates layered in several stages. That is, the positions of the sample reservoirs are shifted from one another in the direction y among the planar plates. It is noted that the separation passages 20 formed in the respective planar plates have lengths which are equal to one another. With this configuration, the sample reservoirs 34 can be inserted therein with the respective electrodes 71, and can be filled therein with the sample.

Figure 8:
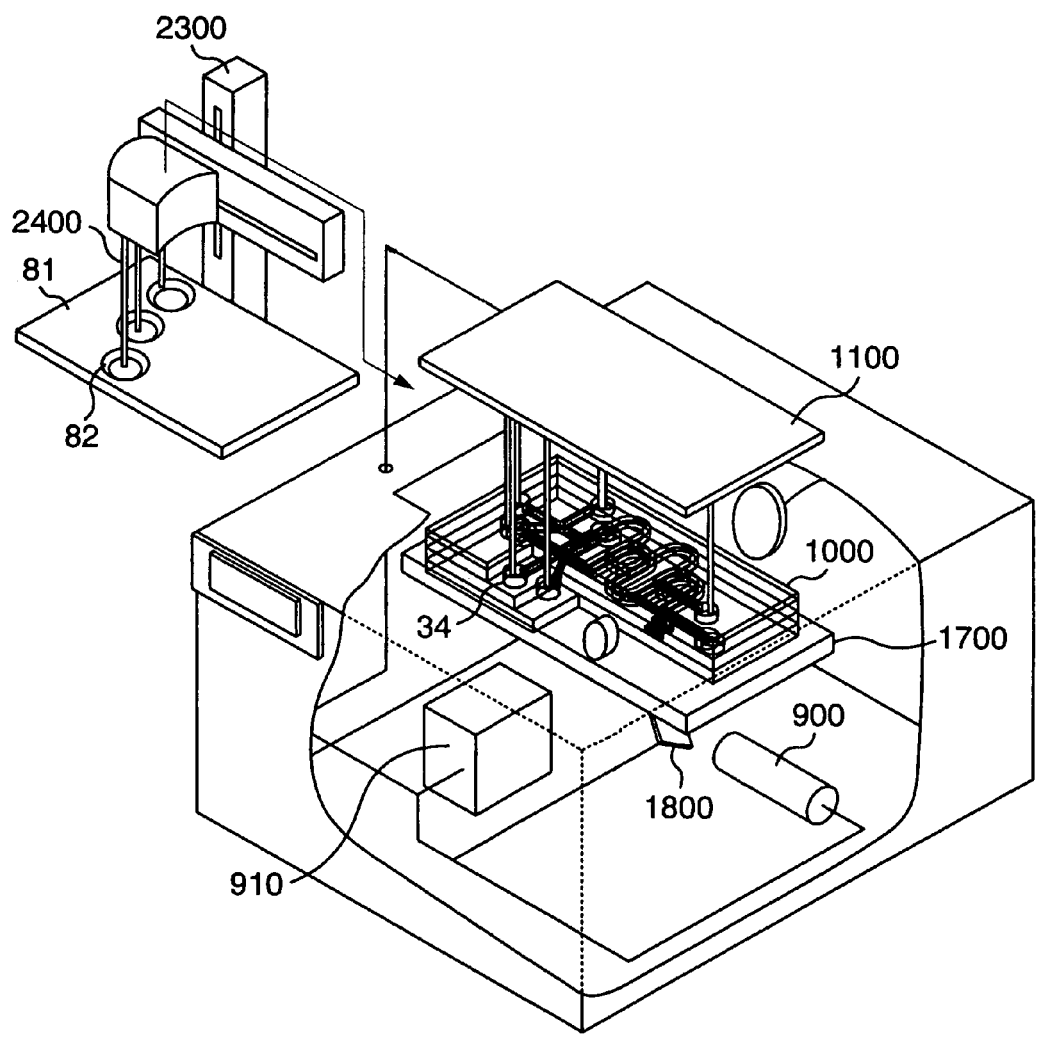
FIG. 8 is a perspective view illustrating the configuration of an example of the electrophoresis apparatus in its entirety.

Referring to FIG. 8 which shows the configuration of the electrophoresis apparatus according to the present invention, a planar plate assembly 1000 composed of planar plates each of which is shown in FIG. 7, and which are layered one another in several stages, is set on a planar base 1700. A titer plate 81 in which several wells 82 reserving therein samples extracted from several specimens are arrayed is set in an automatic sampler 2300. The samples are dripped into the sample reservoirs 34 in the planar plate assembly 1000 by means of sample nozzles 2400 in the automatic sampler 2300. Electrode wires from an electrode assembly 1100 are inserted into the planar plate assembly 1000. An excitation beam from the excitation source 900 is irradiated to the planar plate assembly 1000 in a direction perpendicular to the latter by means of a miller 1800, and fluorescence from the separation channels in the planar plates is detected by a fluorescence detector 910.

In this embodiment, a plurality of planar plates are layered one upon another so that the separation channels in the planar plates are overlapped with each other, and accordingly, a single excitation beam can be led through the separation channels in the planar plates at the same time. With this arrangement, the time of irradiation of the excitation beam becomes longer so that the samples can be sufficiently excited therewith. Since the excitation collecting lens and the fluorescence collecting lens are formed in each of the planar plates, the samples can be efficiently excited without causing scattering and attenuation of fluorescence. Since both irradiation of the excitation beam and detection of fluorescence are simultaneously carried out, time variation of fluorescence from the samples can be detected on a real time base. Thus, satisfactory detection sensitivity can be obtained. In view of the above-mentioned technical effects and advantages, samples from several specimens can be simply and precisely analyzed at a high speed.

Figure 9:
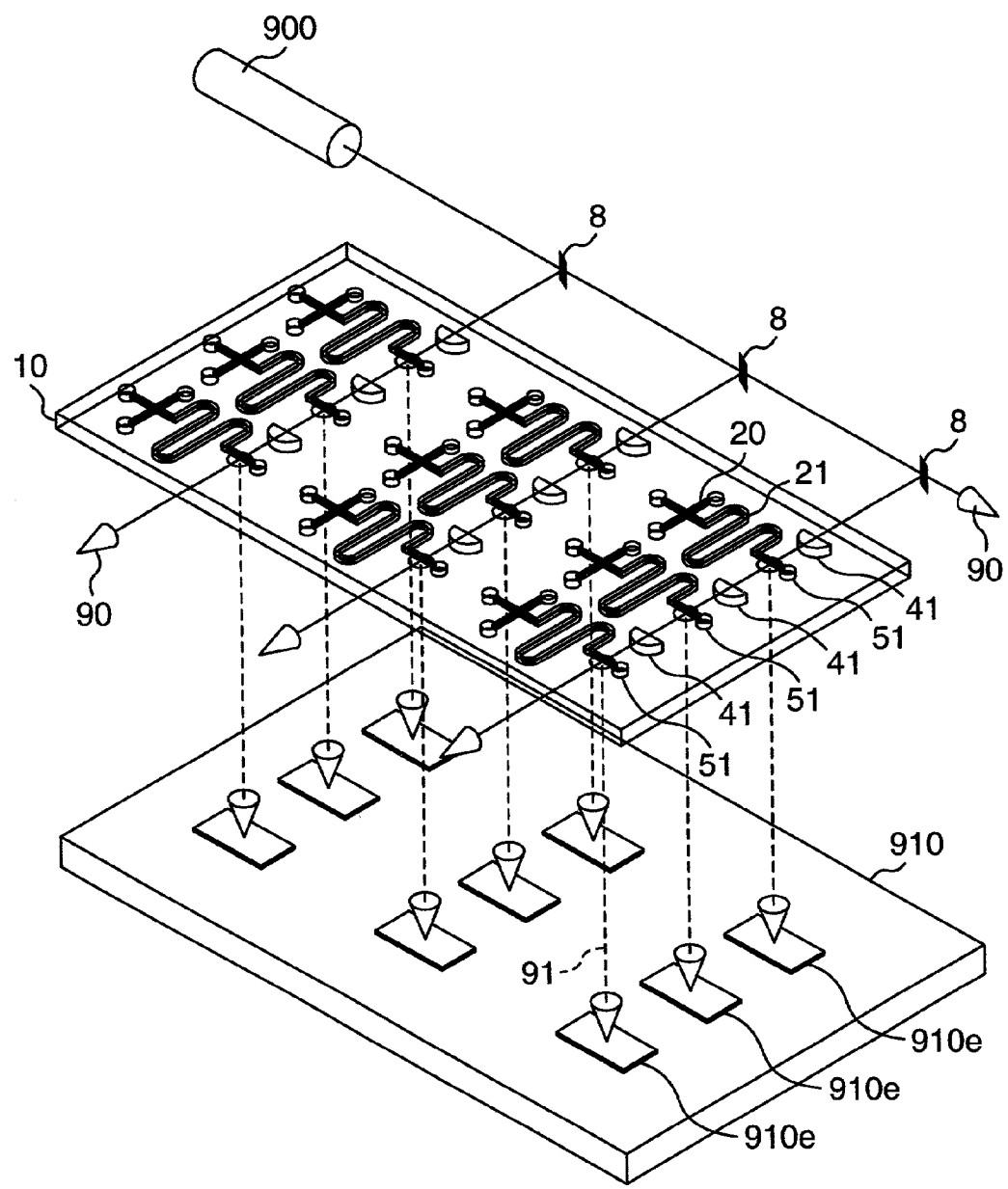
FIG. 9 is a perspective view illustrating a further variant form of the present invention.

FIG. 9 shows a further another variant form of the embodiment of the present invention. In this variant form, several sample channels 20 and separation channels 21 are arrayed in a matrix-like pattern within the planar plate 10. Exciting light converging lenses 41 are provided in the vicinities of side surfaces of the respective separation channels 21 in the planar plate 10, and fluorescence converging lenses 51 are provided for introducing fluorescence from respective samples, outside of the planar plate 10.

Next explanation will be made of the operation of the above-mentioned configuration. Electrical fields are simultaneously changed over from all sample channels 20 into all separation channels 21 so as to simultaneously initiate separation of the respective samples. The excitation beam 90 from the excitation source 900 is split by a half-mirror array 8, and is then led through the excitation focusing lenses 41 so as to irradiate the separation channels 21 through a side surface of the planar plate 10. Fluorescence 91 from the samples is led through the fluorescence collecting lenses 51 so as to be incident upon detection parts 910e on the fluorescence detector 910.

In this variant form, several separation channels are arrayed in a single planar plate while a single excitation beam is led through the several channels at the same time, and accordingly, the time of irradiation becomes longer so that the samples are sufficiently excited. Since the excitation focusing lenses and the fluorescence collecting lenses are formed in the planar plate, the samples can be efficiently excited without causing attenuation and scattering of fluorescence. Both irradiation of the excitation beam and detection of fluorescence are simultaneously carried out so that time variation of fluorescence can be detected on a real time base. Thus, satisfactory detection sensitivity can be obtained. In view of the foregoing technical effects and advantages, samples from several specimens can be simply and precisely analyzed at a high speed.

Since the electrophoresis apparatus according to the present invention comprises a planar plate formed therein with a capillary channel for electrophoretic separation, a light irradiating means for irradiating an excitation beam into a detection part formed in a part of the capillary channel, a fluorescence detecting means for detecting a degree of fluorescence which is generated from a sample by the excitation beam, the capillary channel having a rectangular cross-sectional shape and being composed of a top surface and a bottom surface which are parallel with the surface of the planar plate, and left and right wall surfaces, a first flat and smooth incoming window formed in the bottom surface of the capillary channel, for introducing the excitation bean into the channel, a second flat and smooth incoming window formed on a surface of the planar plate which is opposed to the first incoming window, for introducing an excitation beam into the planar plate, an excitation transmission path formed between the first and second incoming windows, a first flat and smooth outgoing window formed in one of the side surfaces of the of the channel, for emitting fluorescence from the sample, and a second flat and smooth outgoing window formed in a surface of the planar palate at a position opposed to the first outgoing window, for emitting the fluorescence outside of the planar plate, and a fluorescent transmission path between the first outgoing window and the second outgoing window, there may be provided an electrophoresis apparatus which can reduce background light and stray light so as to enhance the detection accuracy.

Further, since a plurality of planar plates each having the configuration as mentioned above are layered one upon another so that the capillary channels in the planar plates are overlapped with each other while a light irradiating means is provided at a position where a single excitation beam can simultaneously led through the capillary channels in the planar plates layered one upon another, and since fluorescence detecting means are provided at positions distant from side surfaces of the planar plates, there may be provided an electrophoresis apparatus which can simply and precisely analyze samples from several specimens at a high speed.

It will be further understood by those skilled in the art that the foregoing description has been made on embodiments of the invention and that various changes and modifications may be made in the invention without departing from the spirit of the invention and scope of the appended claims.

What is claimed is:

1. An electrophoresis apparatus comprising a planar plate formed therein with a channel for electrophoretic separation and with at least one optical lens, filter or grating component, light irradiating means for irradiating an excitation beam into a detection part formed in a part of the channel, fluorescent detecting means for detecting a degree of fluorescence which is generated from a sample by the excitation beam, the channel having a cross-sectional shape and being composed of a top surface and a bottom surface which are parallel with a surface of the planar plate, and left and right side wall surfaces, a first flat and smooth incoming window formed in the bottom surface of the channel, a second flat and smooth incoming window formed on a surface of the planar plate at a position which is opposed to the first incoming window, for introducing an excitation beam into the planar plate, an excitation transmission path formed between the first and second incoming windows, a first flat and smooth outgoing window formed in one of side wall surfaces of the channel, for emitting fluorescence from the sample, and a second flat and smooth outgoing window formed in a surface of the planar plate at a position opposed to the first outgoing window, for emitting the fluorescence outside of the planar plate, and a fluorescent transmission path between the first outgoing window and the second outgoing window, wherein the planar plate has the channel, the at least one lens, filter or grating optical component, the first flat and smooth incoming window, the second flat and smooth incoming window, the excitation transmission path, the first flat and smooth outgoing window, the second flat and smooth outgoing window and the fluorescent transmission path, all integrally-molded therein.

2. An electrophoresis apparatus as claimed in claim 1, wherein said planar plate is formed of a transparent member adapted to serve as said excitation transmission path and said fluorescent transmission path.

3. An electrophoresis apparatus as claimed in claim 1, wherein light converging means is provided to either or each of both said excitation transmission path and said fluorescent transmission path as said at least one optical component.

4. An electrophoresis apparatus as claimed in claim 1, wherein light splitting means is provided in said fluorescent transmission path as said at least one optical component.

5. An electrophoresis apparatus as claimed in claim 1, wherein a spatial filter is provided in said fluorescent transmission path as said at least one optical component.

6. An electrophoresis apparatus as claimed in claim 1, wherein said planar plate is composed of a first planar plate formed through transcription in one batch by means of a transcription mold incorporating a male structure for forming channels at predetermined positions and a male structure for forming the at least one optical component, and a second transparent plate joined to the first planar plate.

7. An electrophoresis apparatus as claimed in claim 6, wherein male and female structures in the transcription mold are fine structures which are formed by optically exposing and then developing a photosensitive resin film.

8. An electrophoresis apparatus as claimed in claim 6, wherein said first planar plate is made of thermosetting resin.

9. An electrophoresis apparatus as claimed in claim 1, wherein a plurality of channels are formed in one and the same plane in said planar plate, light irradiating means is provided at a position where a single excitation beam from said light irradiating means can pass through said plurality of channels at the same time, and said fluorescent detecting means is provided at a position in extension of the outgoing window formed in the surface of the planar plate.

10. An electrophoresis apparatus as claimed in claim 1, comprising at least one access opening for communication of fluid with said channel, wherein the second flat and smooth incoming window for introducing the excitation beam into the planar plate and the at least one access opening are accessible from mutually differing sides of the planar plate.

11. An electrophoresis apparatus as claimed in claim 1, comprising at least one access opening for communication of fluid with said channel, wherein said second flat and smooth outgoing window for emitting the fluorescence outside of the planar plate and the at least one access opening are accessible from mutually differing sides of the planar plate.

12. An electrophoresis apparatus as claimed in claim 1, wherein the fluorescent transmission path is bounded by an air gap on at least two sides thereof within the planar plate.

13. An electrophoresis apparatus as claimed in claim 1, wherein the planar plate has a plurality of substrates including a monolithic substrate having the channel, the at least one lens, filter or grating optical component, the first flat and smooth incoming window, the second flat and smooth incoming window, the excitation transmission path, the first flat and smooth outgoing window, the second flat and smooth outgoing window and the fluorescent transmission path, all integrally-molded therein.

14. An electrophoresis apparatus comprising a planar plate formed therein with a channel for electrophoretic separation and with at least one optical lens, filter or grating component, light irradiating means for irradiating an excitation beam into a detection part formed in a part of the channel, fluorescent detecting means for detecting a degree of fluorescence which is generated from a sample by the excitation beam, the channel being a capillary channel having a top surface and a bottom surface which are parallel with a surface of the planar plate, and left and right side wall surfaces, a first incoming window formed in one of side wall surfaces of the capillary channel, for introducing the excitation beam into the channel, a second incoming window formed on a surface of the planar plate at a position which is opposed to the first incoming window, for introducing an excitation beam into the planar plate, an excitation transmission path formed between the first and second incoming windows, a first outgoing window formed in the bottom surface of the channel, for emitting fluorescence from the sample, and a second outgoing window formed in a surface of the planar plate at a position opposed to the first outgoing window, for emitting the fluorescence outside of the planar plate, and a fluorescent transmission path between the first outgoing window and the second outgoing window, wherein the planar plate has the channel, the at least one lens, filter or grating optical component, the first incoming window, the second incoming window, the excitation transmission path, the first outgoing window, the second outgoing window and the fluorescent transmission path, all integrally-molded therein.

15. An electrophoresis apparatus as claimed in claim 14, wherein said planar plate is formed of a transparent member adapted to serve as said excitation transmission path and said fluorescent transmission path.

16. An electrophoresis apparatus as claimed in claim 14, wherein light converging means is provided to either or each of both said excitation transmission path and said fluorescent transmission path as said at least one optical component.

17. An electrophoresis apparatus as claimed in claim 14, wherein light splitting means is provided in said fluorescent transmission path as said at least one optical component.

18. An electrophoresis apparatus as claimed in claim 14, wherein a spatial filter is provided in said fluorescent transmission path as said at least one optical component.

19. An electrophoresis apparatus as claimed in claim 14, wherein said planar plate is composed of a first planar plate formed through transcription in one batch by means of a transcription mold incorporating a male structure for forming channels at predetermined positions and a male structure for forming the at least one optical component, and a second transparent plate joined to the first planar plate.

20. An electrophoresis apparatus as claimed in claim 19, wherein male and female structures in the transcription mold are fine structures which are formed by optically exposing and then developing a photosensitive resin film.

21. An electrophoresis apparatus as claimed in claim 19, wherein said first planar plate is made of thermosetting resin.

22. An electrophoresis apparatus as claimed in claim 14, wherein a plurality of channels are formed in one and the same plane in said planar plate, light irradiating means is provided at a position where a single excitation beam from said light irradiating means can pass through said plurality of channels at the same time, and said fluorescent detecting means is provided at a position in extension of the outgoing window formed in the surface of the planar plate.

23. An electrophoresis apparatus as claimed in claim 14, comprising at least one access opening for communication of fluid with said channel, wherein the second incoming window for introducing the excitation beam into the planar plate and the at least one access opening are accessible from mutually differing sides of the planar plate.

24. An electrophoresis apparatus as claimed in claim 14, comprising at least one access opening for communication of fluid with said channel, wherein said a second outgoing window for emitting the fluorescence outside of the planar plate and the at least one access opening are accessible from mutually differing sides of the planar plate.

25. An electrophoresis apparatus as claimed in claim 14, wherein the fluorescent transmission path is bounded by an air gap on at least two sides thereof within the planar plate.

26. An electrophoresis apparatus as claimed in claim 14, wherein the planar plate has a plurality of substrates including a monolithic substrate having the channel, the at least one lens, filter or grating optical component, the first incoming window, the second incoming window, the excitation transmission path, the first outgoing window, the second outgoing window and the fluorescent transmission path, all integrally-molded therein.

27. An electrophoresis apparatus comprising a planar plate formed therein with a channel for electrophoretic separation, light irradiating means for irradiating an excitation beam into a detection part formed in a part of the channel, fluorescent detecting means for detecting a degree of fluorescence which is generated from a sample by the excitation beam, the channel having a cross-sectional shape and being composed of a top surface and a bottom surface which are parallel with a surface of the planar plate, and left and right side wall surfaces, a first flat and smooth incoming window formed in the bottom surface of the channel, a second flat and smooth incoming window formed on a surface of the planar plate at a position which is opposed to the first incoming window, for introducing an excitation beam into the planar plate, an excitation transmission path formed between the first and second incoming windows, a first flat and smooth outgoing window formed in one of side wall surfaces of the channel, for emitting fluorescence from the sample, and a second flat and smooth outgoing window formed in a surface of the planar plate at a position opposed to the first outgoing window, for emitting the fluorescence outside of the planar plate, and a fluorescent transmission path between the first outgoing window and the second outgoing window;

wherein a plurality of planar plates, each of which corresponds to said planar plate, are stacked one upon another so that channels in said plurality of planar plates are overlapped with one another, light irradiating means is provided at a position where a single excitation beam from said light irradiating means can be led through the channels in the planar plates layered one upon another, and said fluorescent detecting means is provided at positions in extension of outgoing windows formed in side surfaces of said planar plates stacked one upon another.

28. An electrophoresis apparatus comprising a planar plate formed therein with a channel for electrophoretic separation, light irradiating means for irradiating an excitation beam into a detection part formed in a part of the channel, fluorescent detecting means for detecting a degree of fluorescence which is generated from a sample by the excitation beam, the channel being a capillary channel having a top surface and a bottom surface which are parallel with a surface of the planar plate, and left and right side wall surfaces, a first incoming window formed in one of side wall surfaces of the capillary channel, for introducing the excitation beam into the channel, a second incoming window formed on a surface of the planar plate at a position which is opposed to the first incoming window, for introducing an excitation beam into the planar plate, an excitation transmission path formed between the first and second incoming windows, a first outgoing window formed in the bottom surface of the channel, for emitting fluorescence from the sample, and a second outgoing window formed in a surface of the planar plate at a position opposed to the first outgoing window, for emitting the fluorescence outside of the planar plate, and a fluorescent transmission path between the first outgoing window and the second outgoing window;

wherein a plurality of planar plates, each of which corresponds to said planar plate, are stacked one upon another so that channels in said plurality of planar plates are overlapped with one another, light irradiating means is provided at a position where a single excitation beam from said light irradiating means can be led through the channels in the planar plates layered one upon another, and said fluorescent detecting means is provided at positions in extension of outgoing windows formed in side surfaces of said planar plates stacked one upon another.

* * * * *